United States Patent [19]

Briggs et al.

[11] Patent Number: 5,868,712
[45] Date of Patent: Feb. 9, 1999

[54] PUMP WITH DOOR-MOUNTED MECHANISM FOR POSITIONING TUBING IN THE PUMP HOUSING

[75] Inventors: Kenneth D. Briggs, San Jose; Russel M. Sampson, Mountain View, both of Calif.

[73] Assignee: Abbott Laboratories, Abbott Park, Ill.

[21] Appl. No.: 873,662

[22] Filed: Jun. 12, 1997

[51] Int. Cl.[6] ................................................. A61M 1/00
[52] U.S. Cl. ............................... 604/153; 417/53; 417/63
[58] Field of Search ................................... 604/153, 152, 604/151, 118–120, 34, 35, 65, 66; 417/53, 63, 4, 474–477, 234

[56] References Cited

U.S. PATENT DOCUMENTS

| | | | |
|---|---|---|---|
| 5,540,561 | 7/1996 | Johnson | 604/153 X |
| 5,586,868 | 12/1996 | Lawless et al. | 417/53 |
| 5,628,731 | 5/1997 | Dodge et al. | 604/153 |

OTHER PUBLICATIONS

Copy of brochure entitled "imed." published by IMED Corporation, Copyright date 1989.
Copy of brochure entitled "Flo–Gard 6301," published by Baxter Healthcare Corporation, Copyright date 1992.

Primary Examiner—John D. Yasko
Attorney, Agent, or Firm—Neal D. Marcus

[57] ABSTRACT

A peristaltic pump is provided with a housing, a pump head in the housing, and a receiving path defined along a housing and pump head for receiving tubing. An air sensor assembly in the pump has a slot for receiving a section of the tubing in the receiving path. A position covering the receiving path and an open position exposing the receiving path. An engaging member is provided for pushing the tubing in the slot. The engaging member is pivotally mounted to the door for rotation about an axis parallel to the door pivot axis. The engaging member has a ram for contacting the tubing. The orientation of the ram relative to the door can change as the ram enters the slot when the door closes so that the tubing is pushed relatively evenly and along a substantially straight line into the slot.

27 Claims, 6 Drawing Sheets

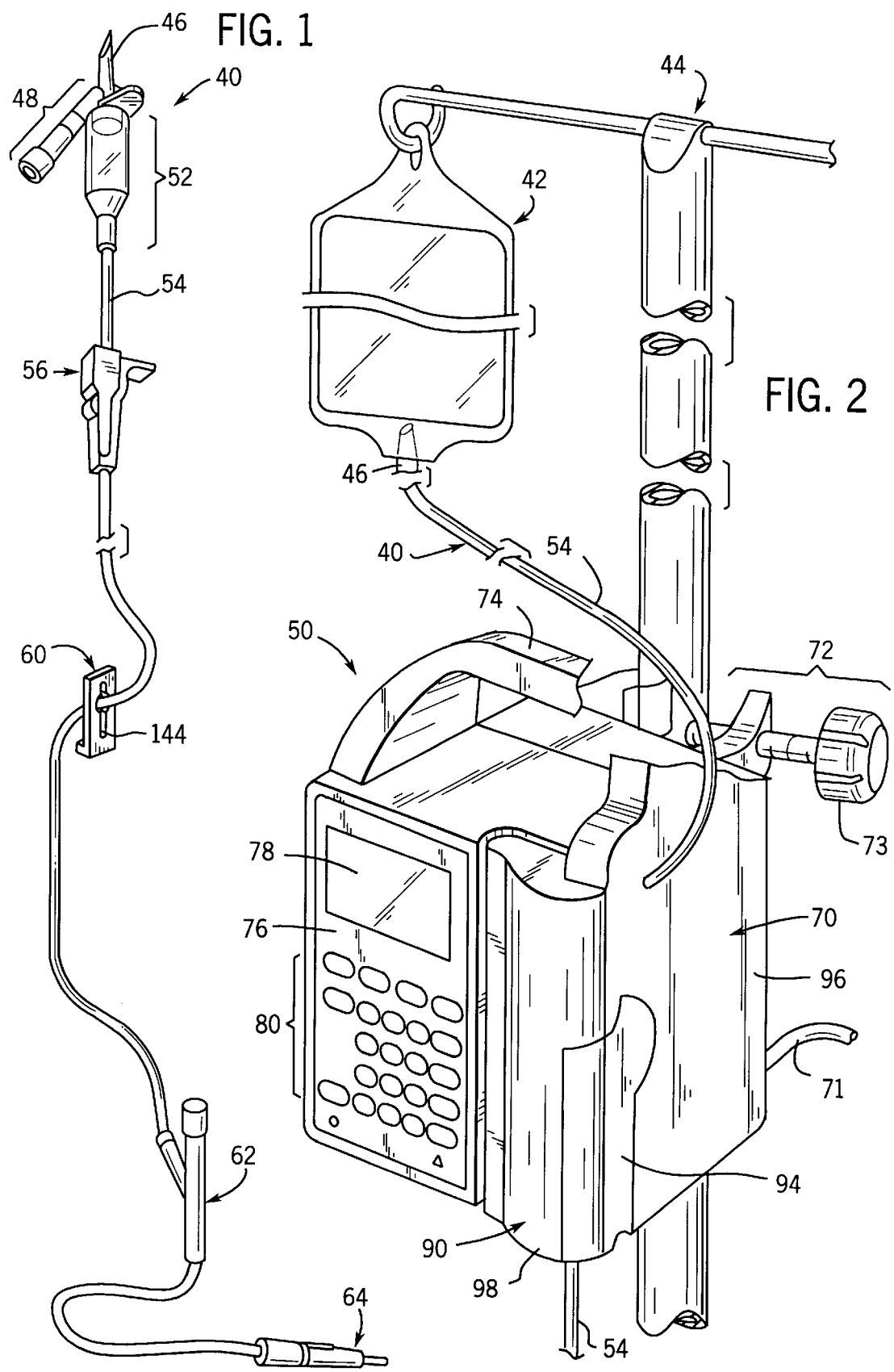

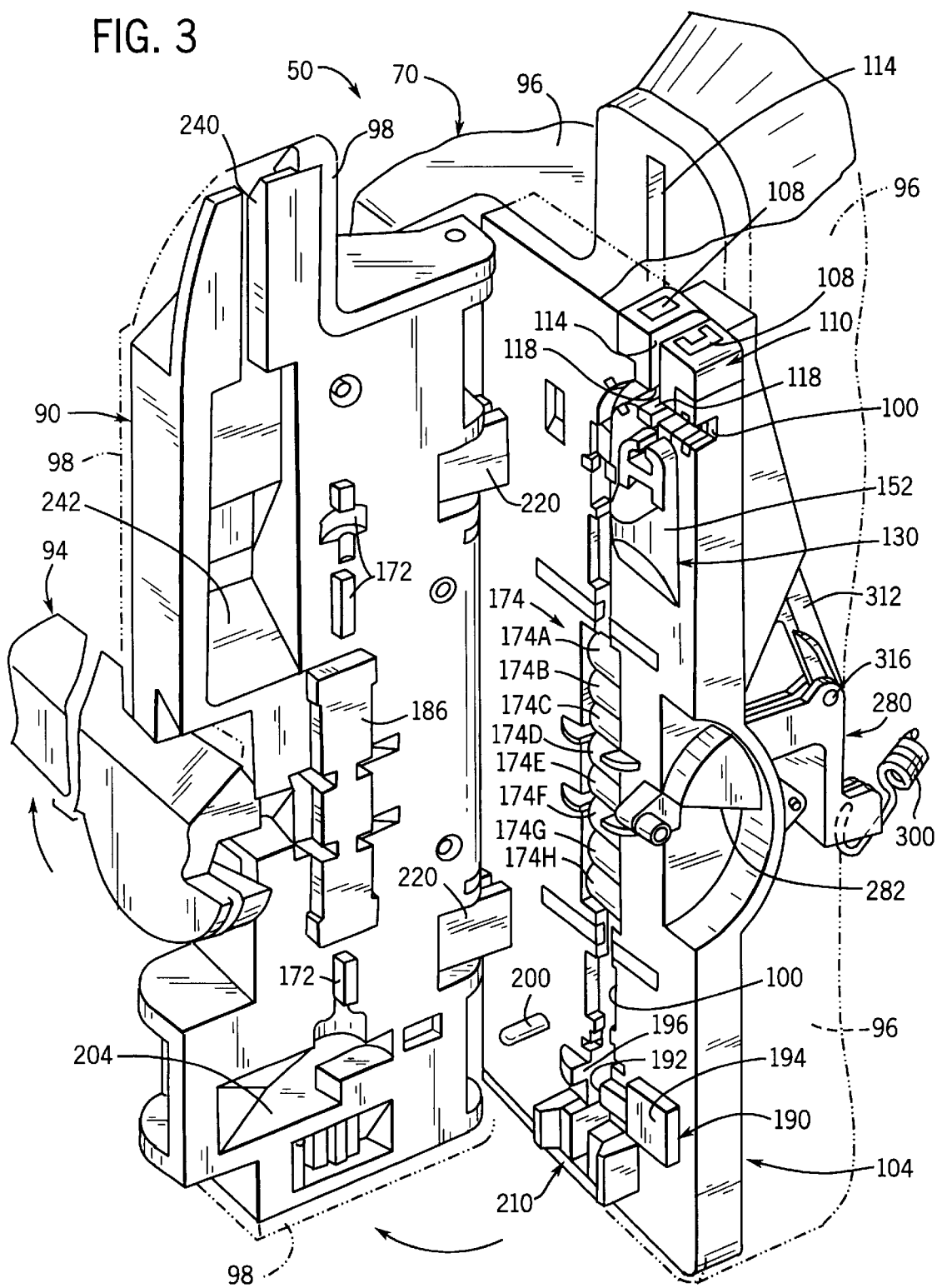

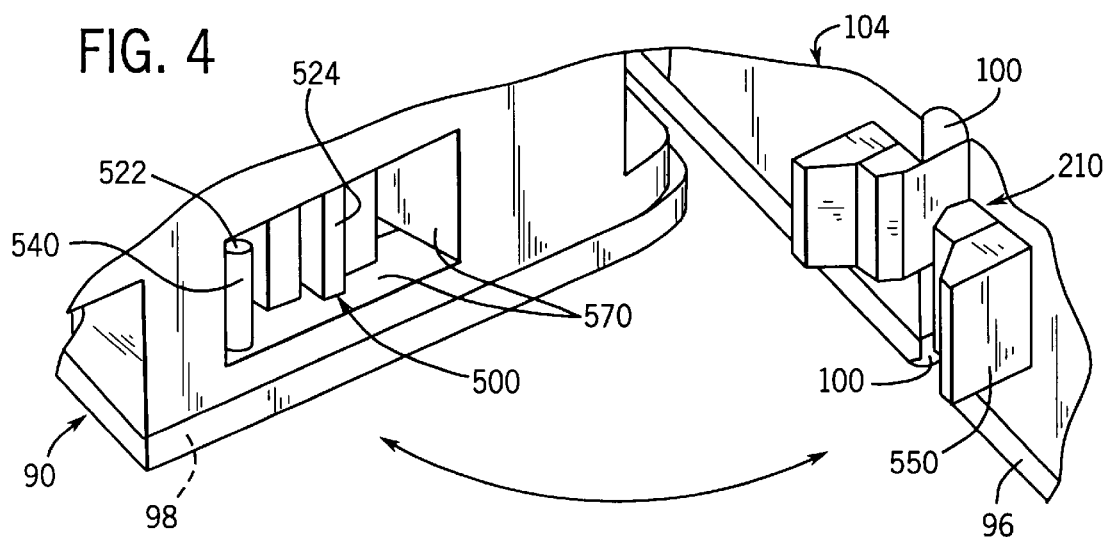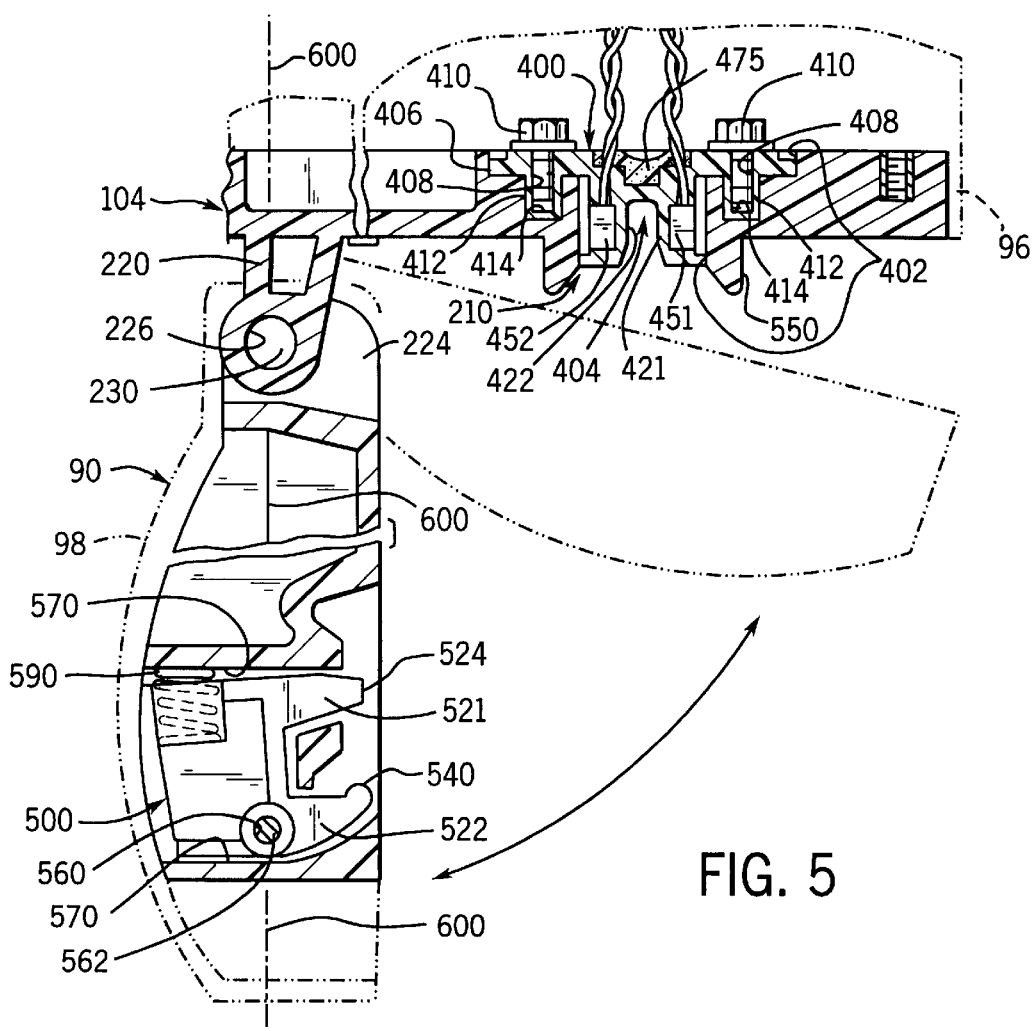

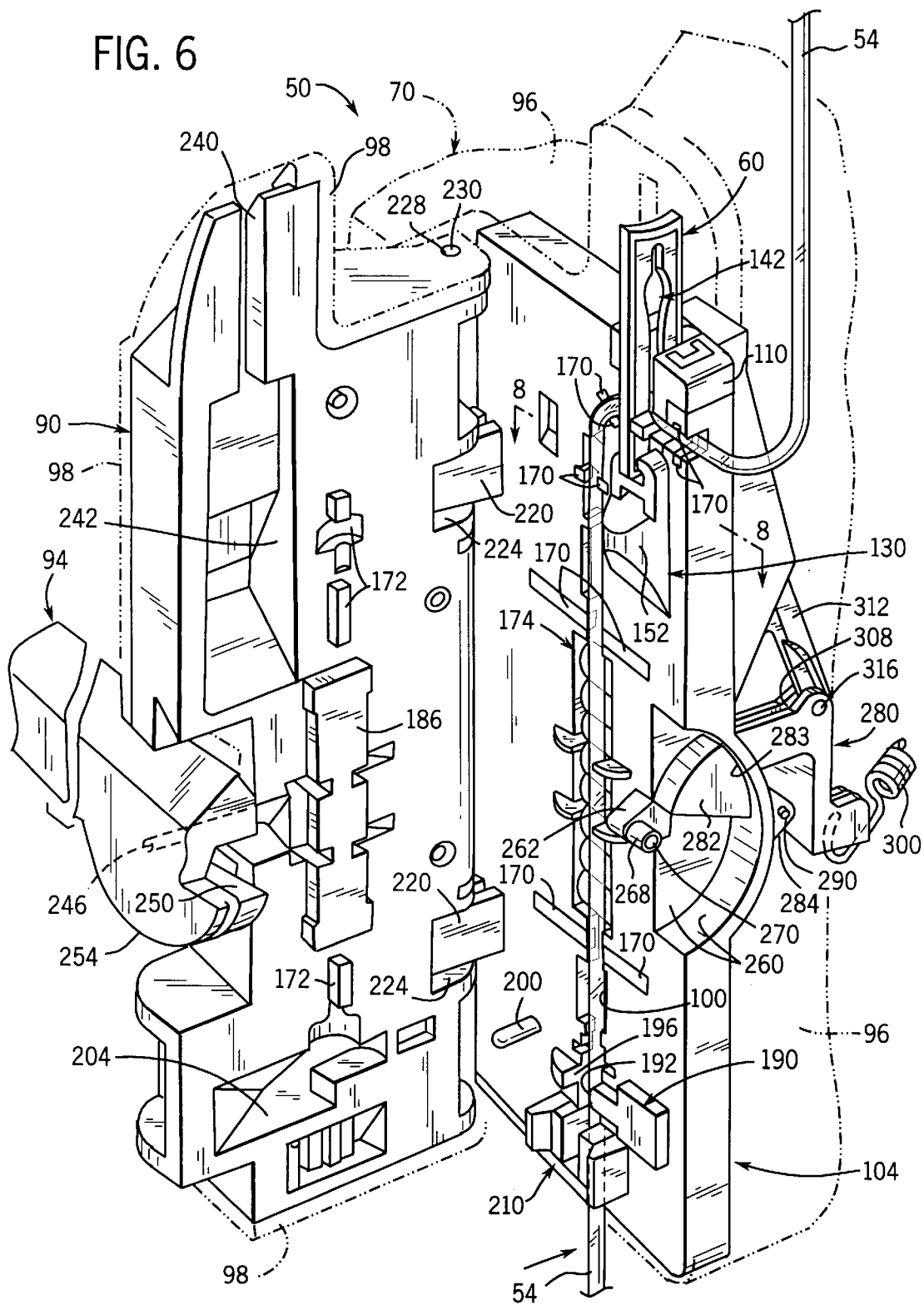

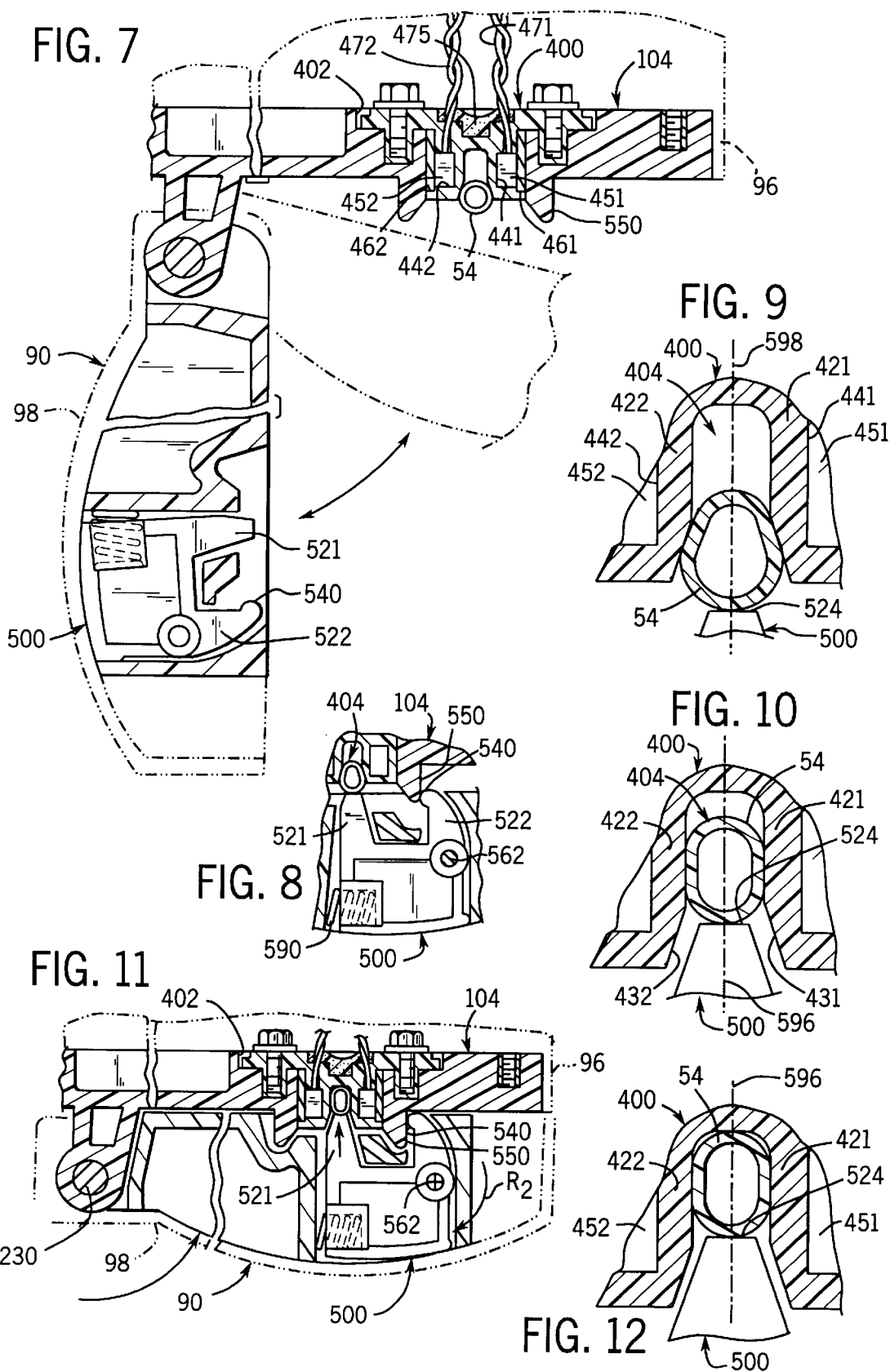

PUMP WITH DOOR-MOUNTED MECHANISM FOR POSITIONING TUBING IN THE PUMP HOUSING

CROSS REFERENCE TO RELATED APPLICATION(S)

Not applicable.

STATEMENT REGARDING FEDERALLY SPONSORED RESEARCH OR DEVELOPMENT

Not applicable.

REFERENCE TO A MICROFICHE APPENDIX

Not applicable.

TECHNICAL FIELD

This invention relates to a liquid delivery system and is especially suitable for use as part of an infusion pump system designed to deliver parenteral and enteral fluids, as well as whole blood or red blood cell components, using a wide variety of standard intravenous administration sets and fluid containers.

BACKGROUND OF THE INVENTION AND TECHNICAL PROBLEMS POSED BY THE PRIOR ART

One conventional type of infusion pump system employs a peristaltic pump in conjunction with an intravenous administration set. The set consists of flexible thermoplastic tubing through which fluid flows from a suspended container, such as a flexible bag or rigid bottle, to a patient's indwelling vein access device, such as a needle or cannula inserted into the patient. A length of the administration set tubing between the fluid container and the patient is mounted in the peristaltic pump which sequentially squeezes adjacent sections of the tubing so as to pump the fluid via a peristaltic action along the tubing into the patient.

To insure that such pumping systems function satisfactorily, such pumping systems typically include a system for sensing air bubbles in the liquid flowing in the tubing in the pump. If the control system senses a sufficient amount of air, then an alarm is actuated and/or the operation of the pump is terminated. The air sensor control system for the pump may permit a small bubble to be pumped through the tubing without actuating the alarm or shutting the pump down, but the control system will actuate an alarm and/or shut down the pump if the rate of small bubble flow exceeds a preselected value. The pump control system will also generate an alarm and/or shut down the pump if the length of a single bubble has a size which exceeds a predetermined length along the tubing.

A conventional air sensor employed in such peristaltic pumps is a piezoelectric transmitter/sensor assembly which has a slot for receiving a length of the tubing. The tubing, which is typically a flexible polyvinyl chloride material, is squeezed lightly between the opposed walls of the slot. In the piezoelectric transmitter/sensor assembly, there is a piezoelectric transmitter transducer in one of the walls, and there is a piezoelectric receiving transducer in the other wall.

The piezoelectric transmitter transducer is electrically powered to produce mechanical vibrations. The mechanical vibration is transmitted as ultrasonic energy through the wall of the tubing into the liquid. At the receiving side of the slot, the energy passes from the liquid through the wall of the tubing and into the receiving transducer. The ultrasonic energy is attenuated, scattered, or reflected dependent upon the conditions within the fluid. At the wall opposite the transmitter transducer, the receiver transducer converts the energy into an electrical signal which varies as a function of the energy transmission through the liquid. This signal can be correlated as function of the presence or absence of an air bubble.

If the wall of the tubing is not in good contact with the sides of the slot in the sensor assembly, then the transmission of the ultrasonic energy from the transmitter transducer into and through the wall of the tubing will be degraded. Similarly, there will be a degradation of the ultrasonic energy at the other side of the slot as the energy passes from the tubing wall to the receiving transducer. The signal is greatly attenuated owing to the poor contact between the tubing and the walls of the sensor slot, and this results in the generation of a smaller electrical signal. A sufficiently small signal could be of the same, small magnitude that would occur if there was an air bubble in the fluid. Thus, the control system would provide a false alarm and/or shut down the pump. In view of this, it would be desirable to provide a system in such a pump for facilitating the proper loading of the tubing within the air sensor slot so as to minimize the possibility of false alarms arising from poor contact between the tubing and slot walls.

One type of conventional pump has a door which is pivotally mounted to the pump housing for movement between (1) a closed position covering the tubing in the pump, and (2) an open position which permits loading or unloading of the tubing. Initially, the tubing can be manually loaded in the pump with a length of the tubing pushed at least part way into the air sensor slot. The inside of the pump door has a projecting finger. When the door is closed, the projecting finger engages the tubing and pushes it further into the air sensor slot to ensure good contact between the wall of the tubing and both of the opposed walls of the air sensor slot.

While the above-described, door-mounted pusher finger may function generally satisfactorily, it would be desirable to provide an improved system for ensuring proper positioning of the tubing within the air sensor slot. In particular, it would be especially advantageous to provide a tubing-engaging system which could be mounted on a door and which could accommodate an offset location of the door pivot axis with respect to the air sensor slot. Such an improved system should accommodate engagement of the tubing in the air sensor slot by the door in such a way that the tubing is contacted, and moved further inwardly into the slot, along a path of movement that does not urge the tubing against the slot walls with unequal force or in a manner that would tend to push part of the tubing away from one of the walls and toward the other wall.

The present invention provides an improved pump system which can accommodate designs that have the above-discussed benefits and features, which is convenient to use, and which is cost-effective with respect to its manufacture and operation. The system is especially suitable for use in a peristaltic pump. However, the system is applicable to other types of pumps that have a tubing-receiving slot which can be covered with a door.

The system is easily operated and can be used with a wide variety of standard administration sets and fluid containers. The system is designed to meet the growing demand for hospital-wide standardization, as well as alternate-site, in-home healthcare standardization.

SUMMARY OF THE INVENTION

The improved system of the present invention accommodates safe delivery of fluids to a patient. The system is convenient to operate and is easy to set up.

The system permits the use of a door on the pump which is pivotally mounted to the pump housing along an axis which is substantially offset from the tubing-receiving path in the housing. The system functions, upon closing the door, to engage the tubing in the air sensor slot and properly seat the tubing in the slot. This eliminates, or greatly minimizes, the likelihood that the tubing may be improperly loaded in the air sensor slot. Thus, during operation, there will be good contact between the air sensor and the tubing so that the possibility of generating low signal false alarms is substantially minimized, if not eliminated.

According to the present invention, a pump includes a housing defining a slot for receiving the tubing through which the fluid is pumped. A door is pivotally mounted on the housing to pivot between a closed position covering the slot and an open position away from the slot. A pusher means is pivotally mounted to the door for pushing the tubing in the slot.

According to yet another aspect of the invention, the housing contains a sensor assembly defining a slot for receiving tubing through which fluid is pumped. A door is pivotally mounted to the housing on a first axis to swing between (i) a closed position covering the slot, and (ii) an open position spaced away from the slot. An engaging member for pushing the tubing in the slot is pivotally mounted to the door for rotation about a second axis. The engaging member has a ram for contacting the tubing whereby the orientation of the ram relative to the door can change as the ram enters the slot when the door closes.

In a preferred embodiment of the invention, the engaging member includes a cam follower in addition to the ram. The housing defines a cam surface. A spring acts between the engaging member and door for biasing the engaging member to pivot about an axis relative to the door. This urges the cam follower against the cam surface as the door is moved to the closed position. This causes the ram to be oriented so as to enter the slot along a path of motion which is generally parallel to the slot walls.

Numerous other advantages and features of the present invention will become readily apparent from the following detailed description of the invention, from the claims, and from the accompanying drawings.

BRIEF DESCRIPTION OF THE DRAWINGS

In the accompanying drawings that form part of the specification, and in which like numerals are employed to designate like parts throughout the same, FIG. 1 is a perspective view of a primary, intravenous administration set;

FIG. 2 is a fragmentary, perspective view of an infusion pump that (1) incorporates features of the present invention, and (2) is mounted on an infusion stand supporting a flexible bag container connected to the administration set which is shown in FIG. 1 and which is illustrated in FIG. 2 as loaded in the infusion pump;

FIG. 3 is an enlarged, fragmentary, perspective view of the front of the infusion pump shown in FIG. 2, and FIG. 3 shows the door in the full open position and the administration set tubing removed from the pump;

FIG. 4 is a fragmentary, greatly enlarged, perspective view of a lower portion of the pump shown in FIG. 3;

FIG. 5 is an enlarged, fragmentary, crosss-sectional view taken generally along the view designation 5—5 in FIG. 3, and FIG. 5 shows the pump chassis in cross-section but for ease illustration, omits detailed structure in the housing behind the chassis;

FIG. 6 is a fragmentary, perspective view similar to FIG. 3, but FIG. 7 shows the administration set tubing loaded into the pump;

FIG. 7 is a view similar to FIG. 5, but FIG. 7 shows the tubing partially loaded into the air sensor slot in the pump;

FIG. 8 is a fragmentary, cross-sectional view similar to FIG. 7, but FIG. 8 shows the door moved toward the closed position where the engaging member in the door is beginning to engage the tubing;

FIG. 9 is a greatly enlarged, fragmentary, cross-sectional view similar to FIG. 8;

FIG. 10 is a view similar to FIG. 9, but FIG. 10 shows the position of the tubing after the door has been moved further toward the fully closed position;

FIG. 11 is a view similar to FIG. 7, but FIG. 11 shows the door in the fully closed position; and FIG. 12 is a greatly enlarged, fragmentary, cross-sectional view similar to FIG. 11, and FIG. 12 shows the air sensor receiving slot region after the door is fully closed;

DESCRIPTION OF THE PREFERRED EMBODIMENT

Figure 13:
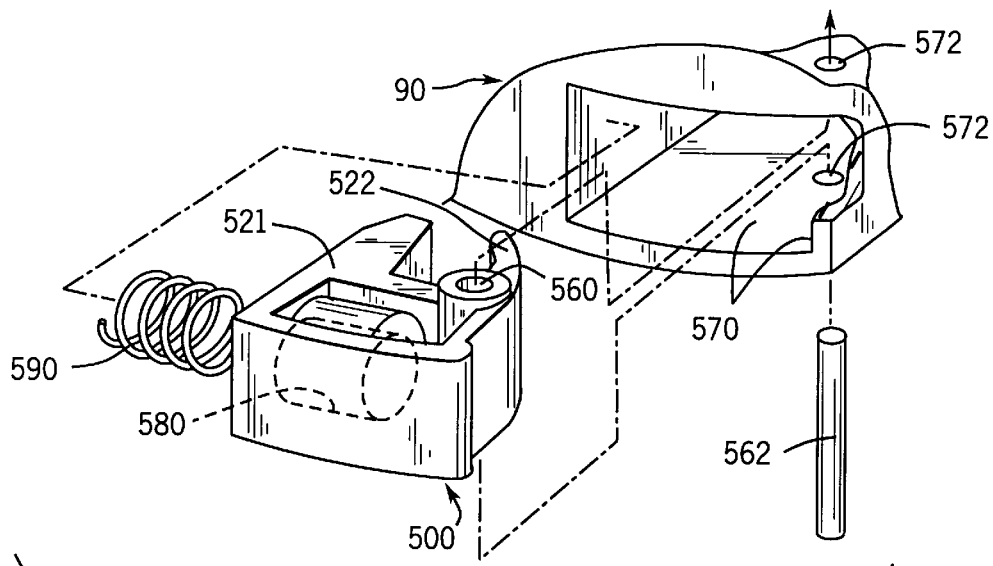
FIG. 13 is a fragmentary, exploded, perspective view of a portion of the pump door tubing engaging member, pivot pin, and biasing spring.

While this invention is susceptible of embodiment in many different forms, this specification and the accompanying drawings disclose only one specific form as an example of the invention. The invention is not intended to be limited to the embodiment so described, however. The scope of the invention is pointed out in the appended claims.

For ease of description, a pump incorporating features of this invention is described in one normal (upright) orientation, and terms such as upper, lower, horizontal, etc., are used with reference to this orientation. It will be understood, however, that the pump of this invention may be stored, transported, and sold in an orientation other than the orientation described.

Figures illustrating the pump show some mechanical elements that are known and that will be recognized by one skilled in the art. The detailed descriptions of such elements are not necessary to an understanding of the invention, and accordingly, are herein presented only to the degree necessary to facilitate an understanding of the novel features of the present invention.

The pump incorporating features of this invention is used with certain conventional components the details of which, although not fully illustrated or described, will be apparent to those having skill in the art and an understanding of the necessary functions of such components.

The improved system of the present invention accommodates delivery of a fluid to a patient with a variety of standard, intravenous administration sets, one of which is illustrated in FIG. 1 and is designated generally therein by the reference numeral 40. The administration set 40 is typically employed to deliver parenteral fluids, enteral fluids, whole blood, red blood cell components, and the like from a fluid container, such as a bottle or such as a flexible bag 42 which is shown in FIG. 2 supported on an intravenous administration stand 44. A portion of the administration set 40 is engaged by a peristaltic pump 50, and a distal portion of the administration set 40 downstream of the pump 50 can be connected to a patient's indwelling vein access device, such as a needle or cannula (not illustrated) which is inserted into the patient.

The container 42 may be of any suitable conventional or special design. The detailed design and specific structure of the container 42 form no part of the present invention.

The administration set 40 may be of any appropriate conventional or special design. The set 40 illustrated in FIG. 1 is a primary, vented, intravenous set sold in the U.S.A. under the designation No. 1881 by Abbott Laboratories, 100 Abbott Park Road, Abbott Park, Ill. 60064-3500, U.S.A. The administration set 40 has a proximal end defined by a hollow, piercing pin 46 projecting from a conventional bacterial retentive air filter 48 at the upper end of a drip chamber 52. A length of hollow, flexible tubing 54 extends from the bottom of the drip chamber 52 through a roller clamp 56 of the type sold by Abbott Laboratories under the designation CAIR.

Disposed on the tubing 54 downstream of the roller clamp 56 is a slide clamp 60 of the type sold by Abbott Laboratories under the designation DUO SLIDE. The DUO SLIDE clamp 60 is described in more detail hereinafter.

A conventional Y-injection site 62 is provided on the tubing 54 downstream of the slide clamp 60. The distal end of the tubing 54 is provided with a conventional male adaptor 64. The adaptor 64 is designed to be attached to a venipuncture device.

The administration set components may be of any suitable special or conventional design, the details of which form no part of the present invention except that some features of a preferred embodiment of the invention are designed to accommodate, and cooperate with, conventional, flexible tubing 54.

As shown in FIG. 2, the pump 50 includes a housing 70 and a rearwardly projecting mounting clamp 72 by which the pump 50 can be mounted to the stand 44. The clamp 72 includes a manually operable knob 73. A convenient carrying handle 74 projects upwardly from the top of the housing 70. Electric power is provided through the rear of the pump via a power cord 71.

The pump 50 has a front panel 76 containing a liquid crystal display screen device 78 and a key pad 80. Next to the front panel 76 is a front door 90 on which is mounted a door handle 94. As shown in FIG. 3, the door 90 can be opened about 90° by initially pivoting the handle 94 from a substantially vertical orientation (as shown in FIG. 2) to a substantially horizontal orientation (as shown in FIG. 3) to unlatch the door 90 from the housing 70, and then swinging the door 90 outwardly.

In FIG. 3, the open pump 50 is shown with the tubing 54 removed so as to better illustrate the details of the pump structure. Further, as seen in FIG. 3, the housing 70 includes an exterior covering or shell 96 which is partly shown in phantom by dashed lines so as to reveal interior details.

Similarly, in FIG. 3, the door 90 has an exterior cover or shell 98 which is shown partly in phantom by dashed lines to better illustrate interior details.

As shown in FIGS. 3 and 6, the open face of the pump housing 70 defines a receiving path 100 for receiving the administration set tubing 54 which is shown loaded in the pump housing 70 in FIG. 6. The receiving path 100 is defined along a generally planar, front, inside face of the open pump housing 70. In particular, the pump 50 includes a block or chassis 104 (FIGS. 3–6) which may be characterized as generally defining a part of the housing 70 to which other pump components are mounted. The chassis 104 includes various cavities and apertures for receiving such other components which are mounted to the chassis or which coact with the chassis 104 as described in detail hereinafter.

As shown in FIG. 3, the receiving path 100 in the upper right-hand corner of the chassis 104 is oriented generally horizontally and opens outwardly to the right-hand side of the pump 50 through the exterior shell 96. The exterior shell 96 thus defines an inlet portion of the receiving path 100, and the exterior shell 96 may be characterized as also generally forming part of the pump housing 70.

Although not part of the present invention, a movable slide clamp carrier 130 (FIGS. 3 and 6) is preferably provided at the upper end of the pump for cooperation with the receiving path 100 and with other features at the upper end of the pump. Specifically, the upper right-hand corner of the chassis 104 defines upwardly projecting posts 108 to which are mounted an insert block or skirt 110. The front of the skirt 110 defines a vertical groove 114 which communicates with the horizontal portion of the tubing receiving path 100 as can be seen in FIG. 3. The skirt 110 has an inwardly extending notch 118 along the vertical groove 114, and the notch 118 defines a part of the receiving path 100 in the face of the pump.

The bottom of the notch 118 at the front of the skirt 110 form bottom portions of the tubing receiving path 100 on either side of the vertical groove 114. The vertical groove 114 extends upwardly into the housing 70 above the skirt 110 as illustrated in FIG. 3.

The chassis 104 is adapted to receive a carrier 130 for holding the tubing slide clamp 60. The carrier 130 has cross slots adapted to receive and hold the slide clamp 60 in a generally vertical orientation as illustrated in FIG. 6. The slide clamp 60 defines an elongate aperture 142 (FIG. 6) having a lower, narrow portion 144 and having an upper, wide portion (FIG. 1).

Prior to insertion of the tubing 54 and slide clamp 60 into the pump 50, the clamp 60 is initially disposed on the tubing 54 in an orientation wherein the tubing 54 is located in the narrow portion 144 of the clamp aperture 142 so as to be squeezed into a closed configuration occluding flow therethrough. The slide clamp 60 is adapted to accommodate subsequent movement downwardly relative to the tubing 54 after the clamp 60 is inserted into the carrier 130.

The slide clamp carrier 130 is adapted to initially receive and hold the clamp 60 at an elevated or raised position as shown in FIGS. 3 and 6 wherein the narrow part 144 of the clamp aperture 142 is around the tubing 54 to squeeze the tubing closed. The carrier 130 is adapted to be subsequently moved to a lowered position (not shown) wherein the wide part of the clamp aperture 142 is around the tubing to permit flow. The mechanisms for effecting movement of the carrier 130 between the upper, elevated position and the lowered position are described hereinafter.

Movement of the carrier 130 downwardly from the elevated position (illustrated in FIG. 6) to the lowered position carries the slide clamp 60 downwardly relative to the tubing 54 which is held in the tubing receiving path on the ledges 120 above the carrier 130 and which becomes positioned in the wide portion of the clamp aperture 142.

When the slide clamp 60 is first fully inserted into the carrier 130, the tubing 54 is received within the channel defining the receiving path 100 on either side of the vertical groove 114. The chassis 104 includes pairs of opposed tabs 170 (FIG. 6) which project slightly into the channel of the receiving path 100 so as to grip the tubing 54 by effecting a small, local deformation of the tubing adjacent the tabs 170. The tabs 170 are preferably separately molded insert pieces which are mounted in appropriate receiving cavities within the chassis 104. A number of such pairs of confronting tabs .170 are provided along the receiving path 100 as shown in FIGS. 3 and 6.

A peristaltic pump head 174 is disposed along the vertical portion of the tubing receiving path 100 as shown in FIGS. 3 and 6. The peristaltic pump head 174 may have any suitable conventional or special configuration. The peristaltic pump head 174 typically comprises a plurality of keys, such as keys 174A–174H, which are sequentially engaged and moved outwardly against the tubing by cam sections on a crank shaft (not visible) which is vertically disposed behind the keys within the pump housing 70. The crank shaft is rotated by a stepping motor (not visible). A platen (FIGS. 3 and 6) 186 is mounted in the door 90 and confronts the tubing 54 adjacent the pump head 174 when the door 90 is closed.

Each pump head key 174A–174H, as it is moved outwardly against the tubing 54, forces the tubing 54 against the platen 186 (FIG. 3) on the closed door 90. The platen 186 is biased toward the pump head 174 by a spring (not visible) acting between the door and the platen 186. As one key 174A–174H is moved outwardly to squeeze the tubing 54 closed against the platen 186, the next, adjacent downstream key is moved outwardly to force the fluid contained within the tube further downstream in the tubing 54 in a peristaltic action. The peristaltic pumping system, including the above-discussed peristaltic pump system elements 174A–174H and platen 186, may be of any suitable conventional or special design. The detailed design and operation of such peristaltic pumping system components, as well as other supporting components, control systems, etc., form no part of the present invention.

The tubing 54 extends below the pump head 174 within the channel defining the tubing receiving path 100. Although not part of the present invention, an anti-flood clamp 190 (FIGS. 3 and 6) is preferably provided below the pump head 174. The tubing 54 extends through the anti-flood clamp 190 near the bottom of the pump.

The anti-flood clamp 190 includes an engaging rib 192 and a laterally extending finger press pad 194 (FIG. 3). Adjacent the engaging rib 192, on one side of the tubing receiving path 100, is an anvil 196 projecting outwardly from the front surface of the chassis 104. The tubing 54 is normally loaded between the anvil 196 and the engaging rib 192 as shown in FIG. 6 when the clamp 190 is open.

A portion of the anti-flood clamp 190 extends behind the chassis 104 and includes a spring-biased, over-center toggle spring latch mechanism (not visible in the figures). Normally, when the pump door 90 is opened, the anti-flood clamp rib 192 is biased to the closed position (not illustrated) and must be first manually opened to permit removal or loading of the tubing 54.

In order to open the clamp 190 at the tubing receiving path 100 between the anvil 196 and the tubing engaging rib 192, the finger press pad 194 is pressed rearwardly toward the chassis 104. When the finger press pad 194 is pushed rearwardly to the point where it is substantially parallel to, and adjacent, the surface of the chassis 104 as shown in FIGS. 3 and 6, the over-center toggle spring latch mechanism behind the chassis 104 holds the anti-flood clamp 190 in the open position—even after the operator's finger is removed from the finger press pad 194. This establishes clearance between the engaging rib 192 and the anvil 196 to accommodate positioning of the tubing 54 between the rib 192 and the anvil 196.

When the anti-flood clamp is in the fully opened position illustrated by solid lines in FIG. 6, a portion of the latch mechanism (not visible behind the chassis 104) is forced forwardly so as to extend a pin 200 from a bore 202 in the face of the chassis 104. When the door 90 is subsequently closed, a portion of the door 90 engages the distal end of the pin 200 and forces it inwardly in the bore 202. Inward movement of the pin 200 (through its attachment to the anti-flood clamp 190 behind the chassis 104) causes the flood clamp 190 to pivot outwardly just beyond the over-center point of the toggle-spring mechanism toward the closed position, but the closed door 90 has a recessed engaging surface 204 which prevents the finger press pad 194 and rib 192 from moving to the fully closed position that would squeeze the tubing closed. This permits fluid flow through the clamp 190 when the door is closed. However, when the door 90 is subsequently opened, the finger pad 194 and rib 192 are free to move completely to the fully closed position under the influence of the toggle-spring mechanism so as to clamp the tubing 54 closed.

The anti-flood clamp 190 described above may be of any suitable special or conventional design. The incorporation of an anti-flood clamp 190, and the detailed design and operation thereof, form no part of the present invention.

In accordance with the present invention, the pump 50 includes an air sensor assembly 210 below the anti-flood clamp 190 as illustrated in FIGS. 3 and 6. The air sensor assembly 210 includes a slot that defines part of the tubing receiving path 100. The detailed design and operation of the air sensor assembly 210 is described in detail hereinafter.

The pump 50 may include other sensors, switches, alarms, etc., as may be suitable or desired, but such other elements form no part of the present invention.

As illustrated in FIG. 3, the inside surface of the door 90 may include a plurality of projections 172 which align with the channel defining the tubing receiving path 100 when the door 90 is closed and which function to push the tubing 54 into the channel defining the receiving path 100.

The tubing 54 can be easily loaded into the above-described tubing receiving path 100 in the pump 50. Typically, before the administration set tubing is loaded into the pump 50, the container 42 (FIG. 2) is connected to the tubing 54. Prior to connecting the tubing 54 to the container 42, the roller clamp 56 (FIG. 1) is first closed to occlude flow through the tubing 54. Then the outlet on the container 42 (FIG. 2) is exposed. The administration set piercing pin 46 (FIG. 1) is then inserted into the outlet of the container 42 with a twisting motion. The container 42 is then suspended from the stand 44, and the drip chamber 52 (FIG. 1) is filled to the score mark.

Before the tubing 54 is loaded into the pump 50, the administration set 40 is primed. With the pump 50 located below the container 42, the roller clamp 56 is opened to expel air from the administration set tubing 54 while the slide clamp 60 located on the tubing is in an open condition so as not to occlude the tubing. The roller clamp 56 is then closed. The male adapter 64 at the distal end of the administration set tubing 54 can then be attached to a venipuncture device. If the venipuncture device is not indwelling, then the device must primed prior to making the venipuncture.

Care should be taken to purge air bubbles from the system. Air is dislodged from the back check valve in the Y-site 62 by inverting and tapping it sharply while fluid is flowing.

Prior to loading the tubing 54 into the pump 50, the operator should verify that the roller clamp 56 is between the container 42 and the slide clamp 60. The operator should also verify that the roller clamp 56 is closed and confirm that there is no flow in the drip chamber 52. Next, the slide clamp 60 is closed by pushing the clamp 60 so that the tubing 54 is squeezed closed in the narrow portion 144 of the clamp aperture.

Then the pump door 90 is opened by lifting the door handle 94. The anti-flood clamp 190, which automatically moves to the closed orientation when the door 90 opens, must be latched open by pushing the finger press pad 194. The clamp 190 will remain open after the operator's finger is removed owing to the action the over-center toggle spring mechanism with the clamp 190 as described above.

The administration set tubing 54 is then positioned along the open face of the pump 50. The slide clamp 60 is aligned with the carrier slots. The slide clamp 60, along with the closed tubing 54 disposed therein, is moved inwardly so as to position the slide clamp 60 within the carrier slots and within the housing vertical groove 114. This results in the portion of the tubing 54 adjacent the slide clamp 60 being received within the channel defined in the tubing receiving path 100 above the carrier 130.

The operator then aligns the remaining portion of the tubing 54 adjacent the remaining portions of the receiving path 100, and the operator loads the tubing 54 within the channel of the receiving path 100 from the top to the bottom of the pump (FIG. 6). Care should be taken so as not to stretch the tubing. The tubing 54 is pressed into the channel defining the receiving path 100 with the pad of a finger tip while avoiding contacting the tubing with sharp objects, such as finger nails.

The door 90 is then closed over the loaded tubing 54, and the handle 94 is latched by pushing it downwardly to the fully closed position illustrated in FIGS. 2 and 11. The inside of the door 90 includes an upper groove 240 (FIGS. 3 and 6) and a cavity or recess 242 (FIGS. 3 and 6) for receiving the outwardly projecting portions-of the slide clamp 60 and carrier 130, respectively, when the door 90 is closed.

Next, before starting the pump 50, the roller clamp 56 above the pump 50 should be opened, and the lack of flow into the drip chamber 52 should be confirmed.

With reference to FIG. 6 (which shows the administration set tubing 54 loaded in the pump 50), it will be appreciated that in the illustrated preferred form of the pump, the tubing receiving path is defined substantially in a plane along the housing 70 (which housing 70 includes the chassis 104 and the top skirt 110 that define the channel of the tubing receiving path 100). The plane in which the loaded tubing 54 lies is generally vertical when the pump is in the normal operating orientation.

The door 90 is preferably mounted on a generally vertical axis for pivoting between the open and closed positions. In the preferred embodiment illustrated, the pivot axis of the door 90 is parallel to the portion of the tubing receiving path 100 defined along the face of the pump head 174. The door pivot axis is also offset forwardly of the tubing receiving path 100.

In particular, the door pivot axis is defined in the chassis 104, as shown in FIGS. 3 and 6, by a pair of door pin-receiving projections 220. As illustrated in FIG. 6, the door 90 defines two slots 224 for each receiving one of the chassis projections 220. FIG. 5 shows one of the slots 224. Each of the chassis projections 220 defines a pin-receiving bore 226 (FIG. 5), and the bores 226 are aligned with bores in the door 90, such as an upper bore 228 visible in FIG. 6. An upper pin 230 (visible in FIG. 6) and a lower pin 230 (visible in FIG. 5), are disposed in the chassis projection bores 226 and in the bores in the door 90 for providing a connection accommodating pivoting movement of the door 90.

The door handle 94 pivotally mounted with a pin 246 (FIG. 6) to the door 90 for rotation between the open position (FIG. 6) and the closed position (FIG. 2). The handle 94 includes a latch slot 250 (FIG. 6) and an exterior camming surface 254 (FIG. 6).

As shown in FIG. 6, the housing chassis 104 defines a recessed latch region 260 for receiving the camming surface 254 of the door handle 94. Projecting outwardly from the edge of the chassis 104 adjacent the latch region 260 is a boss 262 (FIG. 6). As shown in FIG. 6, a latch roller 268 is disposed on a pin 270 mounted in the boss 262. When the door 90 is closed, the latch pin 270 and roller 268 are received in the slot 250 of the handle 94. As the handle 94 is rotated about the handle pivot pin 246 (in the counter-clockwise direction as viewed in FIG. 6), the handle latch slot 250 slides along the roller 268 until the handle 94 is in the fully closed orientation as shown in FIG. 2. Owing to (1) a curvature of the latch slot 250, and (2) the relative positions of the door handle pivot pin 246 and the latch pin roller 268, the resiliency of the system (especially as may be provided by the spring-biased platen 186 in the door 90) creates an over-center toggle latch action holding the door handle 94 in the fully closed position to maintain the door 90 latched closed.

The carrier 130 (FIG. 6) has previously been described as being movable between an elevated position (FIG. 6) and a lowered position (not shown). The movement of the door handle 94 to the latched closed position (illustrated in FIG. 2) effects movement of the carrier 130 between the elevated and lowered positions by a linkage mechanism which is next described. In particular, the exterior camming surface 254 on the door handle 94 is designed to engage a cam follower element or crank 280 (FIG. 6). The crank 280 defines a cam follower surface 282. As shown in FIG. 6, the portion of the crank 280 defining the cam follower surface 282 extends through a slot 283 in a portion of the chassis 104 which defines the recessed latch region 260. The crank 280 is pivotally mounted to the back of the chassis 104 adjacent the recessed latch region 260. As can be seen in FIG. 6, the chassis 104 has a rearwardly projecting, mounting boss 284, and the boss 284 defines a bore 286 for receiving a pin 290. The crank 280 is pivotally mounted on the pin 290.

As shown in FIG. 6, the crank 280 includes a slot 296 and a bridging rib 298. As shown in FIGS. 6, one end of a helical coil tension spring 300 is connected to crank 280, and the other end of the spring 300 is connected to the chassis (at a location not visible in the figures). The spring 300 normally biases the crank 280 in a counterclockwise direction as viewed in FIG. 6 so as to position the crank cam follower surface 282 outwardly in the recessed latch region 260 when the door handle 94 is in the unlatched or open orientation (FIG. 6).

As shown in FIG. 6, the crank 280 defines a slot 308 which is adapted to receive one end of a link or arm 312 which is pivotally connected to the crank 280 by means of a pin 316.

The link or arm 312 extends upwardly, and the upper end of the arm 312 (not visible in FIG. 6) extends up through the rear portion of the skirt 110 and is partially pivotally connected to a rear portion of the carrier 130 projecting rearwardly through a slot in the chassis 104.

It will be appreciated that when the door 90 is open, the spring 300 pulls the crank 280 to pivot the crank 280 counterclockwise as viewed in FIGS. 6. This holds the arm 312 and carrier 130 in the elevated position which accommodates insertion or removal of the slide clamp 60. On the other hand, when the door 90 is shut and the door handle 94 is latched closed as explained in detail above, the door handle camming surface 254 engages the cam follower surface 282 of the crank 280 and causes the crank 282 to pivot clockwise. This pulls the carrier 130 (and slide clamp 60 disposed therein) downwardly so as to position the wide part of the clamp aperture 142 around the tubing 54 and permit flow through the tubing. Subsequently, when the door handle 94 is unlatched and lifted upwardly toward the position illustrated in FIG. 6, the spring 300 again causes the crank 280 and arm 312 to return the carrier 130 (and slide clamp 60 carried therein) to the elevated position (FIGS. 6).

When the carrier 130 is returned to the elevated position (FIG. 6), the slide clamp 60 can be removed. It will be appreciated that when the carrier 130 is in the elevated position, the slide clamp 60 is oriented on the tubing 54 in the receiving path such that the tubing 54 is squeezed closed in the narrow portion 144 of the clamp aperture 142. Hence, whenever the door 90 is opened to permit removal of the slide clamp 60, the tubing 54 is always squeezed closed by the slide clamp 60. Thus, if medical personnel fail to close the roller clamp 56 (FIG. 1) prior to removing the tubing 54 from the pump, then there will be no danger of fluid free flowing into the patient even if the lower clamp 190 is opened and the tubing 54 is removed from the pump.

If desired, the pump 50 could be alternatively designed so as to eliminate the above-described movable carrier 130 and linkage mechanism for effecting movement thereof. In such an alternate design, the tubing 54 would just be loaded into the receiving path 100 without locating the slide clamp 60 within the pump. The above-discussed carrier 130 and linkage mechanism for moving it in the pump 50 form no part of the present invention.

The air sensor assembly 210 is illustrated in greater detail in FIGS. 4–12. The air sensor assembly 210 includes a housing 400 which, in the preferred embodiment, is a separately molded piece inserted in an aperture 402 in the main pump housing chassis 104 as shown in FIG. 5. It will be appreciated, however, that the sensor assembly housing 400 could alternatively be provided as a unitary part of the chassis 104 which is regarded as a part of the main pump housing.

As shown in FIG. 4, the tubing receiving path 100 extends through, and is defined in part by, the sensor assembly 210. To this end, the sensor assembly housing 400 defines a slot 404 (FIG. 5) which is a part of the channel-like, tubing-receiving path 100 defined by the pump chassis 104 above and below the air sensor assembly 210. Because the sensor assembly housing 400 is inserted in the pump housing chassis 104, the slot 404 may be characterized as being defined generally by the main housing of the pump. In the preferred embodiment illustrated in FIG. 5, where in the air sensor assembly housing 400 is a separately molded piece inserted in the chassis 104 in the main pump housing, the slot 404 may also be characterized as being more specifically defined by the air sensor assembly housing 400 per se.

The rear portion of the air sensor assembly housing 400 includes a laterally extending mounting portion 406 (FIG. 5) which defines a pair spaced-apart bores 408 for each receiving a screw 410 threadingly engaged with a threaded insert 412 mounted in a bore 414 in the chassis 104.

As shown in FIG. 9, the air sensor assembly housing 400 includes a first wall 421 and a second wall 422 spaced from the first wall 421. The air sensor assembly housing slot 404 is defined between the first wall 421 and the second wall 422. The walls 421 and 422 are preferably parallel and define facing, parallel surfaces along the sides of the slot 404.

As shown in FIG. 10, the air sensor assembly housing slot 404 is further defined by a first planar outer wall 431 extending at an oblique angle from the first wall 421 and by a second planar outer wall 432 extending at an oblique angle from the second planar wall 422. The distance between the first and second planar outer walls 431 and 432, respectively, increases with increasing distance from the first and second parallel walls 421 and 422. The oblique walls 431 and 432 facilitate insertion of the tubing 54 into the slot 404.

As illustrated in FIG. 9, air sensor assembly housing 400 defines a first cavity 441 and a second cavity 442. A transmitting transducer 451 is disposed in the first cavity 441. A receiving transducer 452 is disposed in the second cavity 442. As shown in FIG. 7, the transducer 451 is covered with a layer of epoxy 461 across the opening of the cavity 441. Similarly, the transducer 452 is covered with a layer of epoxy 462 at the opening of the cavity 442.

As shown in FIG. 7, electrical lead wires 471 from the transducer 451 extend rearwardly through an aperture at the rear of the housing 400. Similarly, electrical lead wires 472 extend rearwardly from the transducer 452 through an aperture in the rear of the housing 400. The lead wires 471 and 472 are connected to the sensing and control circuit forming part of the pump sensing and control system. The rear portion of the housing 400 adjacent the rearwardly extending electrical lead wires 471 and 472 is sealed with a suitable epoxy material 475 (FIGS. 5 and 7).

As described hereinafter in detail, the tubing 54 is initially loaded and seated between the walls 421 and 422 of the housing 400 as shown in FIG. 12. The tubing 54 is lightly compressed laterally so as to establish good contact between the tubing 54 and the housing slot walls 421 and 422. The transmitting transducer 451 may be of any suitable conventional or special type (e.g., piezoelectric) for transmitting ultrasonic energy through the first wall 421, through the adjacent wall of the tubing 54, through the liquid contained in the tubing 54, through the far wall of the tubing 54, and through the housing second wall 422. The transmitted energy is sensed by the receiving transducer 452 which may be of any suitable conventional or special type (e.g., piezoelectric).

When the pump is operating to pump liquid through the tubing 54, the transducers 451 and 452 can be operated so that the output signal from the receiving transducer 452 can be continuously monitored. The output signal from the receiving transducer 452 falls generally within a narrow band or range when the liquid is flowing through the tubing 54 with no entrained air bubbles. However, if air bubbles are present in the liquid flowing through the tubing 54, then the energy transmitted from the first transducer 451 is reflected, scattered, and/or attenuated such that the energy sensed by the receiving transducer 452 is less than the energy received when air bubbles are absent. The output signal from the receiving transducer 452 thus drops as a function of the reduction of the energy transmission owing to the amount of air between the transducers 451 and 452.

The control system for the pump can be adjusted to actuate an alarm and/or terminate pump operation when the output signal from the receiving transducer 452 drops below a predetermined level. Also, the control system may actuate an alarm and/or terminate the pump operation if the output signal from the receiving transducer 452 drops to only a slightly reduced level, but the slightly reduced level of the signal exists continuously, or intermittently, throughout a preselected time period. This would permit a relatively small bubble to pass through the sensor without actuating an alarm or shutting down the pump, but an excessive number of small bubbles in a short period of time would actuate the alarm and/or shut down the pump.

The proper sensing of air bubbles in the liquid flowing through the tubing 54 depends upon the tubing 54 being properly seated within the housing slot 404 between the transducers 451 and 452. If the tubular wall of the tubing 54 does not have good contact with the opposite sidewalls 421 and 422 which define the housing slot 404, then the ultrasonic energy may be scattered, reflected, or otherwise excessively attenuated at the region or regions of poor contact between the tubing 54 and either or both of the slot walls 421 and 422. This can result in the receiving transducer 452 producing a reduced output signal which would be characteristic of air in the liquid flowing through the tubing even when there is no air in the tubing. This will cause a false alarm and/or an unnecessary shutdown of the pump. Consequently, it is desirable to insure that the tubing 54 is properly loaded and seated within the sensor assembly slot 404.

According to the present invention, a novel mechanism is provided to insure that the tubing 54 is properly seated within the sensor assembly slot 404. The mechanism is provided in the door 90 and includes and engaging member 500 (shown removed from the door 90 in FIGS. 13–18 and shown in the door in FIGS. 4 and 5). The engaging member 500 functions, as explained in detail hereinafter, to properly seat the tubing 54 within the sensor assembly housing 400 even though the orientation of the door 90 changes as it approaches the sensor assembly slot 404 (FIG. 5) when the door pivots about the offset pivot axis defined by the door pivot pins 230 (FIG. 5).

The engaging member 500 has a generally U-shaped portion 504 (FIG. 15) which has a first leg 521 and a second leg 522. The first leg 521 has a distal end defining a ram for contacting the tubing 54. The ram includes a distal planar end face 524 (FIG. 15), a first planar side surface 531, and a second planar side surface 532. Each planar side surface 531 and 532 extends from the planar end face 524 at an oblique angle relative to the planar end face 524.

The distal end of the second leg 522 functions as a cam follower and includes a generally semi-cylindrical cam follower surface 540 (FIGS. 7, 8, 9, 14, and 15). The semi-cylindrical cam follower surface 540 is adapted to contact a cam surface 550, which projects perpendicularly outwardly from the face of the housing chassis 104 as shown in FIGS. 4, 5, 7, 8 and 11, as the door 90 closes.

Figure 14:
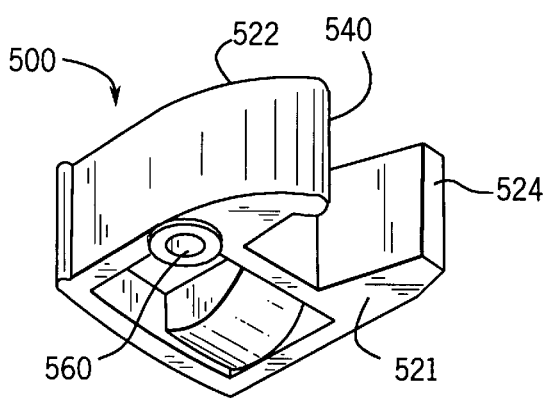
FIG. 14 is a perspective view of the engaging member viewed from the bottom.
Figure 15:
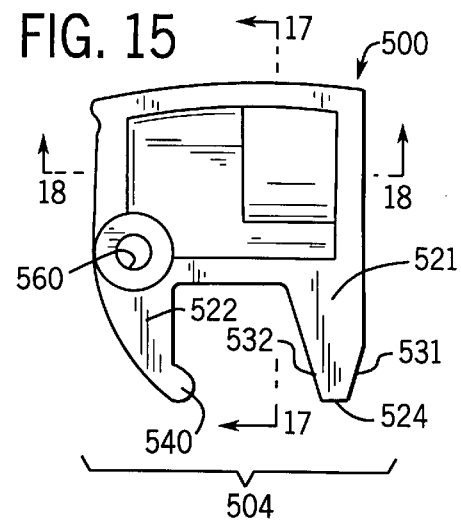
FIG. 15 is a top-plan view of the engaging member.
Figure 16:
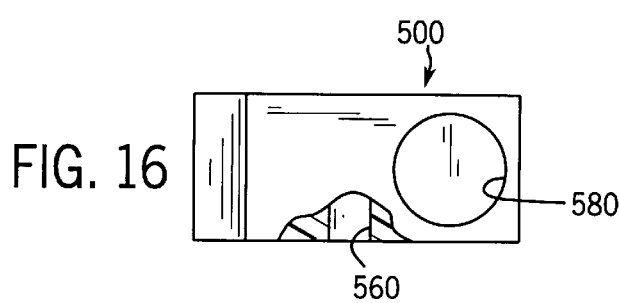
FIG. 16 is a side elevational view of the engaging member shown partly in cross section.
Figure 17:
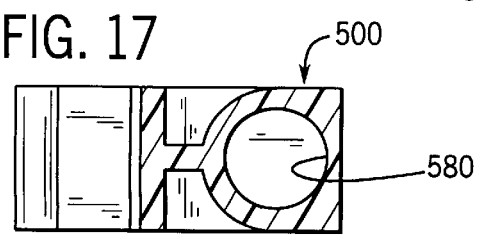
FIG. 17 is a cross-sectional view taken generally along the plane 17—17 in FIG. 15.
Figure 18:
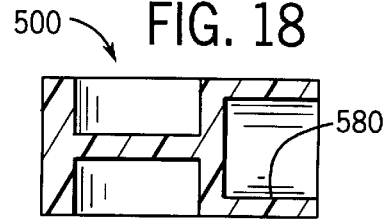
FIG. 18 is a cross-sectional view taken generally along the plane 18—18 in FIG. 15.

As shown in FIGS. 13–15, the engaging member 500 includes a vertical bore 560 adjacent the inner end of the second leg 522. The bore 560 is adapted to receive a pivot pin 562 (FIGS. 5 and 13). The pin 562 pivotally mounts the engaging member 500 in a cavity 570 (FIGS. 4, 5 and 13) in the door 90. To this end, the door 90 includes a pair of aligned bores 572 (FIG. 13) for receiving the pin 562. The pin 562 defines a pivot axis about which the engaging member 500 can pivot relative to the door 90. In the preferred embodiment illustrated, the pivot axis of the engaging member 500 defined by the pin 562 is parallel to the pivot axis of the door 90 defined by the door pivot pins 230 (FIG. 5).

As shown in FIGS. 13, 16, 17 and 18, the engaging member 500 defines a blind bore 580. The bore 580 is adapted to receive a helical coil compression spring 590 (FIGS. 5 and 13). The compression spring 590 acts between the engaging member 500 at the end of the bore 580 and the side of the cavity 570 defined by the door 90. The spring 590 functions to bias the engaging member 500 so as to pivot counterclockwise about the pivot axis defined by the pin 562 as viewed in FIGS. 5 and 13.

The spring 590 biases the engaging member 500 so that the semi-cylindrical cam follower surface 540 moves toward the door pivot axis defined by the pivot pin 230 (FIG. 5). As the door 90 is closed, the cam follower surface 540 engages the outwardly extending cam surface 550 (FIG. 8). The spring 590 insures that the cam follower surface 540 will remain engaged with the cam surface 550 as the door 90 is closed through the final few degrees of rotation to the fully closed position (shown in FIG. 11).

As the door 90 closes and the cam follower surface 540 engages the cam surface 550 (FIG. 8), the engagement between the cam surface 550 and cam follower surface 540 causes the engaging member 500 to pivot clockwise as viewed in FIG. 8 against the biasing force of the spring 590. As the door 90 is moved to the completely latched closed position (FIG. 11), the engaging member 500 is rotated further in the clockwise direction (as viewed in FIG. 11). This has the effect of orienting the engaging member ram on the distal end of the first leg 521 so that it enters the sensor assembly slot 404 relatively straight and is not skewed excessively to one side or the other of the slot 404.

In the preferred embodiment, the ram at the distal end of the first leg 521 moves generally along a straight line into the slot 404 during the last few degrees of door rotation as shown in FIGS. 9–12. The ram planar end face 524 is thus substantially perpendicular to the longitudinal axis 598 of the slot 404 when the end face 524 enters the slot 404 as shown in FIGS. 9–12. The engaging member end face 524 thus contacts the tubing 54 in a manner that applies an inward force against the tubing 54 which is substantially centrally oriented relative to the slot 404. This prevents the engaging member ram end face 524 from exerting a force upon the tubing 54 in a skewed direction that might push the tubing 54 toward an inner corner of the slot in a manner that could lead to poor seating contact between a portion of the tubing and portions of one or both of the slot walls 421 and 422.

FIG. 9 illustrates the tubing 54 initially disposed relatively far outwardly in the slot 404. The tubing 54 may be initially located in such a position if the medical technician does not take proper care in pushing the tubing further inwardly when the tubing is loaded in the pump. However, even if the tubing 54 is initially poorly loaded as shown in FIG. 9, the engaging member 500 will still function according to the present invention to properly seat the tubing 54 within the slot 404 so as to provide good contact between the tubing 54 and the slot sidewalls 421 and 422.

For purposes of further describing certain relationships within the structure of the preferred embodiment of the invention, the door 90 may be characterized as being pivotally mounted about a first axis as defined by the pivot pin 230 (FIG. 5) relative to the pump housing. The engaging member 500 may be characterized as being pivotally mounted about a second axis (defined by the pin 562 in FIG. 5) relative to the door 90. The semi-cylindrical cam follower surface 540 of the engaging member 500 may be characterized as defined about a third axis. In the preferred embodiment, the first axis about which the door 90 pivots is parallel to the second axis about which the engaging member 500 pivots. In the preferred embodiment, the third axis about which the semi-cylindrical cam follower 540 is defined is parallel to both the first axis about which the door 90 pivots and the second axis about which the engaging member 500 pivots.

Further, in the preferred embodiment, the distance between the third axis (the axis about which is defined the cam follower semi-cylindrical surface 540) and the first axis (the door pivot axis) is less than the distance between the second axis (the engaging member pivot axis) and the first axis (the door pivot axis).

Also, in the preferred embodiment, the pump housing may be characterized as having flat, inside surface regions lying in a plane (i.e., the major flat surface regions on the inside face of the pump chassis 104 which are exposed when the pump door 90 is opened as shown in FIGS. 3 and 5). Further, the door 90 preferably has inside, flat surface regions which (a) lie in a plane parallel to both the first axis (the door pivot axis) and the second axis (the engaging member pivot axis), and (b) confront the housing flat, inside surface regions when the door 90 is closed. The distance between the door plane and the first axis (the door pivot axis) as measured along a line perpendicular to the door plane is substantially the same as the distance between the door plane and the second axis (the engaging member pivot axis) as measured along a line perpendicular to the door plane.

Finally, it will be appreciated that in the illustrated preferred embodiment, the first axis (door pivot axis) and the second axis (the engaging member pivot axis) may be characterized as lying in, or defining, a plane 600 (FIG. 5). The compression spring 590 is preferably disposed on one side of the plane 600, and the engaging member ram end face 524 is disposed on the other side of the plane 600.

It will be readily apparent from the foregoing detailed description of the invention and from the illustrations thereof that numerous variations and modifications may be effected without departing from the true spirit and scope of the novel concepts or principles of this invention.

What is claimed is:

1. A pump comprising:
   (1) a housing containing a sensor assembly defining a slot for receiving tubing through which fluid is pumped;
   (2) a door pivotally mounted to said housing on a first axis to swing between (i) a closed position covering said slot, and (ii) an open position spaced away from said slot; and
   (3) an engaging member for pushing said tubing in said slot, said engaging member pivotally mounted to said door for rotation about a second axis, said engaging member having a ram for contacting said tubing whereby the orientation of said ram relative to said door can change as said ram enters said slot when said door closes.

2. The pump in accordance with claim 1 in which said slot is defined at least in part by two, spaced-apart, parallel walls in said sensor assembly.

3. The pump in accordance with claim 2 in which said slot is further defined by a first planar outer wall extending at an oblique angle from one of said parallel walls and by a second planar outer wall extending at an oblique angle from the other of said parallel walls, the distance between said first and second planar outer walls increasing with increasing distance from said parallel walls.

4. The pump in accordance with claim 1 further including a compression spring acting between said door and said engaging member to bias said engaging member to pivot about said second axis relative to said door.

5. The pump in accordance with claim 1 in which
   said housing defines a cam surface;
   said engaging member is generally U-shaped and has first and second legs which each have a distal end;
   said ram is defined by the distal end of said first leg; and
   said engaging member includes a cam follower defined by said second leg adjacent the distal end of said second leg for engaging said cam surface.

6. The pump in accordance with claim 5 in which said cam surface projects outwardly beyond said slot.

7. The pump in accordance with claim 1 in which
   said housing defines a cam surface;
   said engaging member includes a cam follower for engaging said cam surface;
   said slot is defined at least in part by two, spaced-apart, parallel walls; and
   said cam surface includes at least a portion which is parallel to said parallel walls of said slot.

8. The pump in accordance with claim 1 in which
   said housing defines a cam surface;
   said engaging member includes a cam follower for engaging in said cam surface;
   said first axis is parallel to said second axis;
   said cam follower includes a generally semi-cylindrical surface defined about a third axis which is parallel to said first and second axes; and
   the distance between said third axis and said first axis is less than the distance between said second axis and said first axis.

9. The pump in accordance with claim 1 in which
   said first and second axes are parallel;
   said housing has flat surface regions lying in a plane;
   said door has inside flat surface regions which (a) lie in a plane parallel to said first and second axes, and (b) confront said housing flat surface regions when said door is closed; and
   the distance between said door plane and said first axis as measured along a line perpendicular to said door plane is substantially the same as the distance between said door plane and said second axis as measured along a line perpendicular to said door plane.

10. A pump comprising:
    (1) a housing in which is mounted a sensor assembly having two, spaced-apart, parallel walls defining a slot for receiving tubing through which fluid is pumped;
    (2) a door pivotally mounted to said housing on a first axis parallel to said slot to swing between (i) a closed position covering said slot, and (ii) an open position spaced away from said slot;
    (3) an engaging member for pushing said tubing in said slot, said engaging member pivotally mounted to said door for rotation about a second axis parallel to said first axis, said engaging member having (i) a ram for entering said slot and engaging said tubing, and (ii) a cam follower, said housing defining a cam surface; and (4) a spring acting between said engaging member and door for biasing said engaging member to pivot about said second axis relative to said door to urge said cam follower against said cam surface as said door is moved to said closed position whereby said ram is oriented to enter said slot along a path of motion which is generally parallel to said slot walls.

11. The pump in accordance with claim 10 in which said housing has flat surface regions lying in a plane;

said door has inside flat surface regions which (a) lie in a plane parallel to said first and second axes, and (b) confront said housing flat surface regions when said door is closed; and the distance between said door plane and said first axis as measured along a line perpendicular to said door plane is substantially the same as the distance between said door plane and said second axis as measured along a line perpendicular to said door plane.

12. The pump in accordance with claim 10 in which said slot is further defined by a first planar outer wall extending at an oblique angle from one of said parallel walls and by a second planar outer wall extending at an oblique angle from the other of said parallel walls, the distance between said first and second planar outer walls increasing with increasing distance from said parallel walls.

13. The pump in accordance with claim 10 in which said engaging member is generally U-shaped and has first and second legs which each have a distal end;

said ram is defined by the distal end of said first leg; and said cam follower is defined by said second leg adjacent the distal end of said second leg.

14. The pump in accordance with claim 10 in which said cam surface projects outwardly beyond said slot.

15. The pump in accordance with claim 10 in which said slot is defined at least in part by two spaced-apart, parallel walls; and said cam surface includes at least a portion which is parallel to said parallel walls.

16. The pump in accordance with claim 10 in which said cam follower includes a generally semi-cylindrical surface defined about a third axis which is parallel to said first and second axes; and the distance between said third axis and said first axis is less than the distance between said second axis and said first axis.

17. The pump in accordance with claim 10 in which said sensor assembly includes a piezoelectric sensor for sensing air bubbles in liquid flowing through said tubing.

18. The pump in accordance with claim 10 in which said ram includes a distal planar end face and two planar side surfaces extending from said planar end face, each said planar side surface defining an oblique angle relative to said planar end face.

19. The pump in accordance with claim 10 in which said first and second axes lie in a plane;

said spring is a compression spring disposed on one side of said plane; and said ram is disposed on the other side of said plane.

20. The pump in accordance with claim 10 in which said engaging member defines a cavity for receiving said spring.

21. The pump in accordance with claim 10 in which said cam surface is closer to said first axis than is said second axis.

22. A pump comprising:

(1) a housing defining a slot for receiving tubing through which fluid is pumped;

(2) a door pivotally mounted to said housing to pivot between a closed position covering said slot and an open position away from said slot; and (3) pusher means pivotally mounted to said door for pushing said tubing in said slot.

23. The pump in accordance with claim 22 in which said housing contains a sensor assembly having two spaced-apart, parallel walls; and said housing slot for receiving said tubing is defined within said sensor assembly at least in part by said two, spaced-apart, parallel walls.

24. The pump in accordance with claim 22 in which said housing includes a cam surface.

25. The pump in accordance with claim 23 in which said pusher means includes (1) a cam follower for engaging said cam surface, and (2) a ram for contacting said tubing.

26. The pump in accordance with claim 23 further including a spring acting between said housing and said pusher means so as to pivot said pusher means to engage said cam follower with said cam surface when said door closes.

27. The pump in accordance with claim 22 in which said door pivots about a first axis and said pusher means pivots about a second axis which is parallel to said first axis.

\* \* \* \* \*